(12) United States Patent
Steinfeld et al.

(10) Patent No.: US 9,402,595 B2
(45) Date of Patent: Aug. 2, 2016

(54) SYSTEMS AND METHODS FOR POSITIONING DETECTOR HEADS

(71) Applicant: General Electric Company, Schenectady, NY (US)

(72) Inventors: Sergio Steinfeld, Tirat Carmel (IL); Avi Bar-Shalev, Tirat Carmel (IL); Yaron Hefetz, Kibbutz Alonim (IL); Gil Kovalski, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 330 days.

(21) Appl. No.: 14/167,321

(22) Filed: Jan. 29, 2014

(65) Prior Publication Data

US 2015/0208999 A1    Jul. 30, 2015

(51) Int. Cl.
  *G01T 1/20*   (2006.01)
  *A61B 6/00*   (2006.01)
  *G01T 1/161*  (2006.01)
  *G01T 1/16*   (2006.01)
  *A61B 6/03*   (2006.01)

(52) U.S. Cl.
  CPC .................. *A61B 6/547* (2013.01); *A61B 6/037* (2013.01); *A61B 6/4258* (2013.01); *A61B 6/4266* (2013.01); *G01T 1/16* (2013.01); *G01T 1/161* (2013.01)

(58) Field of Classification Search
  CPC .................................... G01T 1/61; G01T 1/166
  USPC .......................... 250/363.01, 363.02, 363.04
  See application file for complete search history.

(56) References Cited

U.S. PATENT DOCUMENTS

| | | | |
|---|---|---|---|
| 5,825,031 A * | 10/1998 | Wong et al. | ............... 250/363.03 |
| 6,140,650 A | 10/2000 | Berlad | |
| 6,239,438 B1 | 5/2001 | Schubert | |
| 6,748,044 B2 | 6/2004 | Sabol et al. | |
| 6,943,355 B2 | 9/2005 | Shwartz et al. | |
| 7,026,623 B2 | 4/2006 | Oaknin et al. | |

(Continued)

OTHER PUBLICATIONS

Meikle et al., "Accelerated EM reconstruction in total-body PET: potential for improving tumour detectability," 1994, Physics in Medicine and Biology, vol. 39, pp. 1689-1704.

(Continued)

*Primary Examiner* — David Porta
*Assistant Examiner* — Meenakshi Sahu
(74) *Attorney, Agent, or Firm* — Dean D. Small; The Small Patent Law Group, LLC.

(57) ABSTRACT

An imaging system is provided including a plurality of detector units and a controller. The plurality of detector units are distributed about a bore. The bore is configured to accept an object to be imaged, and the detector units are radially articulable within the bore. The controller is operably coupled to the plurality of detector units and configured to control the positioning of the detector units. The controller is configured to position an external group of the plurality of detector units at a predetermined intermediate position corresponding to a ring having a radius corresponding to a total number of detector units, and to position an internal group of the plurality of detector units radially inside the ring.

24 Claims, 9 Drawing Sheets

(56) References Cited

U.S. PATENT DOCUMENTS

| | | | |
|---|---|---|---|
| 7,242,002 B2 * | 7/2007 | Blevis et al. | 250/363.05 |
| 7,381,959 B2 | 6/2008 | Manjeshwar et al. | |
| 7,671,331 B2 | 3/2010 | Hefetz | |
| 2002/0148970 A1 * | 10/2002 | Wong et al. | 250/394 |
| 2002/0191828 A1 | 12/2002 | Colbeth et al. | |
| 2005/0145797 A1 | 7/2005 | Oaknin et al. | |
| 2006/0108532 A1 * | 5/2006 | Ohana et al. | 250/363.04 |
| 2007/0018108 A1 | 1/2007 | Kitamura | |
| 2008/0011954 A1 * | 1/2008 | Hefetz | 250/363.02 |

OTHER PUBLICATIONS

Riddell et al., "Noise reduction in oncology FDG PET images by iterative reconstruction; a quantitative assessment," 2001, the Journal of Nuclear Medicine, vol. 42, No. 9, pp. 1316-1323.

Shepp et al., Maximum likelihood reconstruction for emission tomography, 1982, IEEE Transaction on Medical Imaging, vol. MI-1, No. 2, pp. 113-121.

Park et al., "Performance of a high-sensitivity dedicated cardiac SPECT scanner for striatal uptake quantification in the brain based on analysis of projection data," Med. Phys. 40(4), Apr. 2013.

* cited by examiner

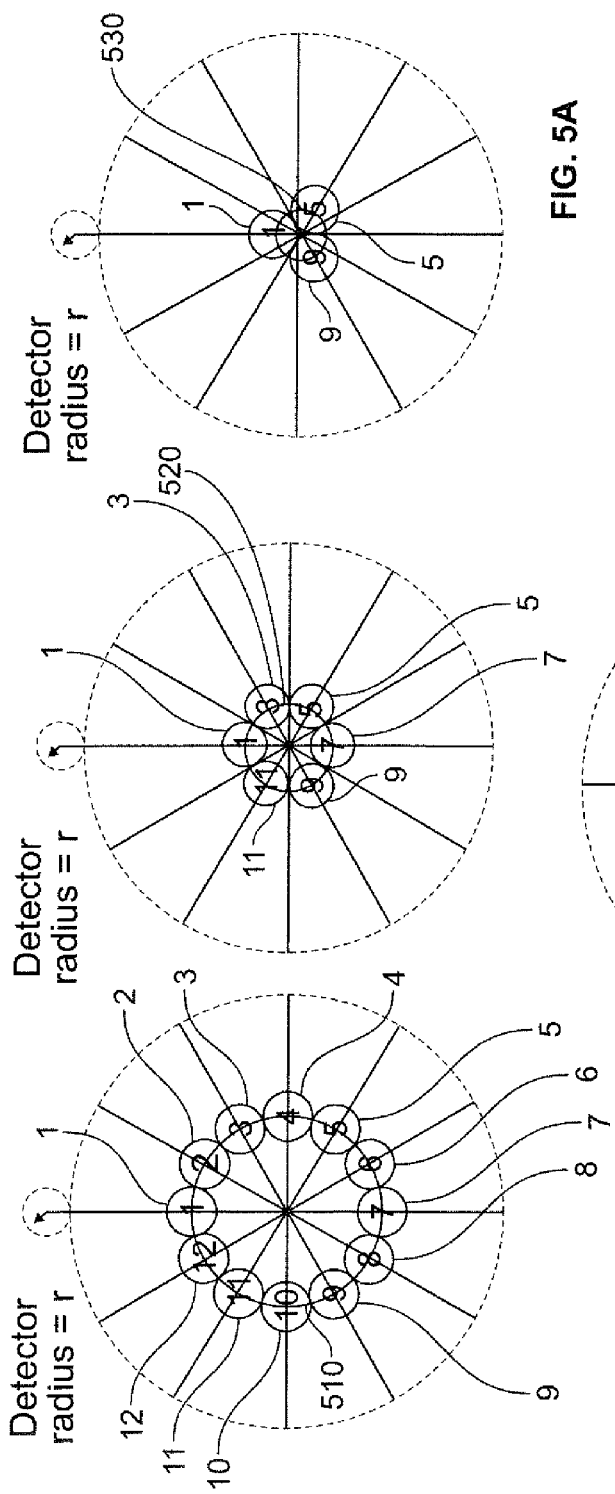
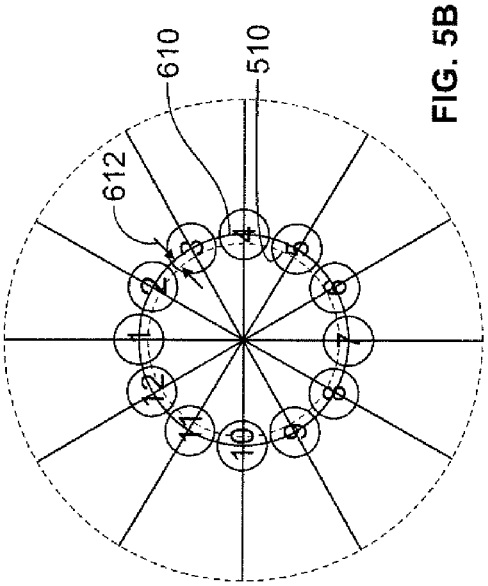
FIG. 5A
FIG. 5B

SYSTEMS AND METHODS FOR POSITIONING DETECTOR HEADS

BACKGROUND OF THE INVENTION

The subject matter disclosed herein relates generally to apparatus and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data, which is used to generate a three-dimensional (3D) image of the subject.

Single Photon Emission Computed Tomography (SPECT) systems may have moving detector heads, such as gamma detectors positioned to focus on a region of interest. For example, a number of heads may be moved (e.g., rotated) to different angular positions for acquiring image data. The acquired image data is then used to generate the 3D images.

Resolution of gamma detectors is a convolution of the detector resolution (mainly pixel size) and the collimator resolution. Collimator resolution degrades with the distance of the collimator from the subject. As a result of the configuration of these systems, including the detectors and collimators, the detector heads often have to be placed at a distance from the subject, for example to avoid collisions between detector heads as the heads are advanced toward a patient or other object to be imaged. Positioning of the detector heads as the detector heads are radially advanced may result in reduced image quality for detectors that are overly far away from a patient, and/or collisions between detectors as the detectors are positioned, and/or inconvenient lengths of set up time to position the detectors.

BRIEF DESCRIPTION OF THE INVENTION

In one embodiment, an imaging system is provided that includes a plurality of detector units and a controller. The plurality of detector units are distributed about a bore. The bore is configured to accept an object to be imaged, and the detector units are radially articulable within the bore. The controller is operably coupled to the plurality of detector units and configured to control the positioning of the detector units. The controller is configured to position an external group of the plurality of detector units at a predetermined intermediate position corresponding to a ring having a radius corresponding to a total number of detector units, and to position an internal group of the plurality of detector units radially inside the ring.

In another embodiment, a method is provided for positioning a plurality of detector units within a bore of an imaging system. The detector units are radially articulable within the bore. The method includes positioning an external group of the plurality of detector units at a predetermined intermediate position corresponding to a ring having a radius corresponding to a total number of detector units. The method also includes positioning an internal group of the plurality of detector units radially inside the ring.

In another embodiment, a tangible and non-transitory computer readable medium is provided for positioning a plurality of detector units within a bore of an imaging system. The detector units are radially articulable within the bore. The tangible and non-transitory computer readable medium includes one or more computer software modules configured to direct one or more processors to position an external group of the plurality of detector units at a predetermined intermediate position corresponding to a ring having a radius corresponding to a total number of detector units; and to position an internal group of the plurality of detector units radially inside the ring.

BRIEF DESCRIPTION OF THE DRAWINGS

FIGS. 5a and 5b illustrate rings corresponding to intermediate or stopping positions in accordance with an embodiment.

DETAILED DESCRIPTION OF THE INVENTION

Figure 1:
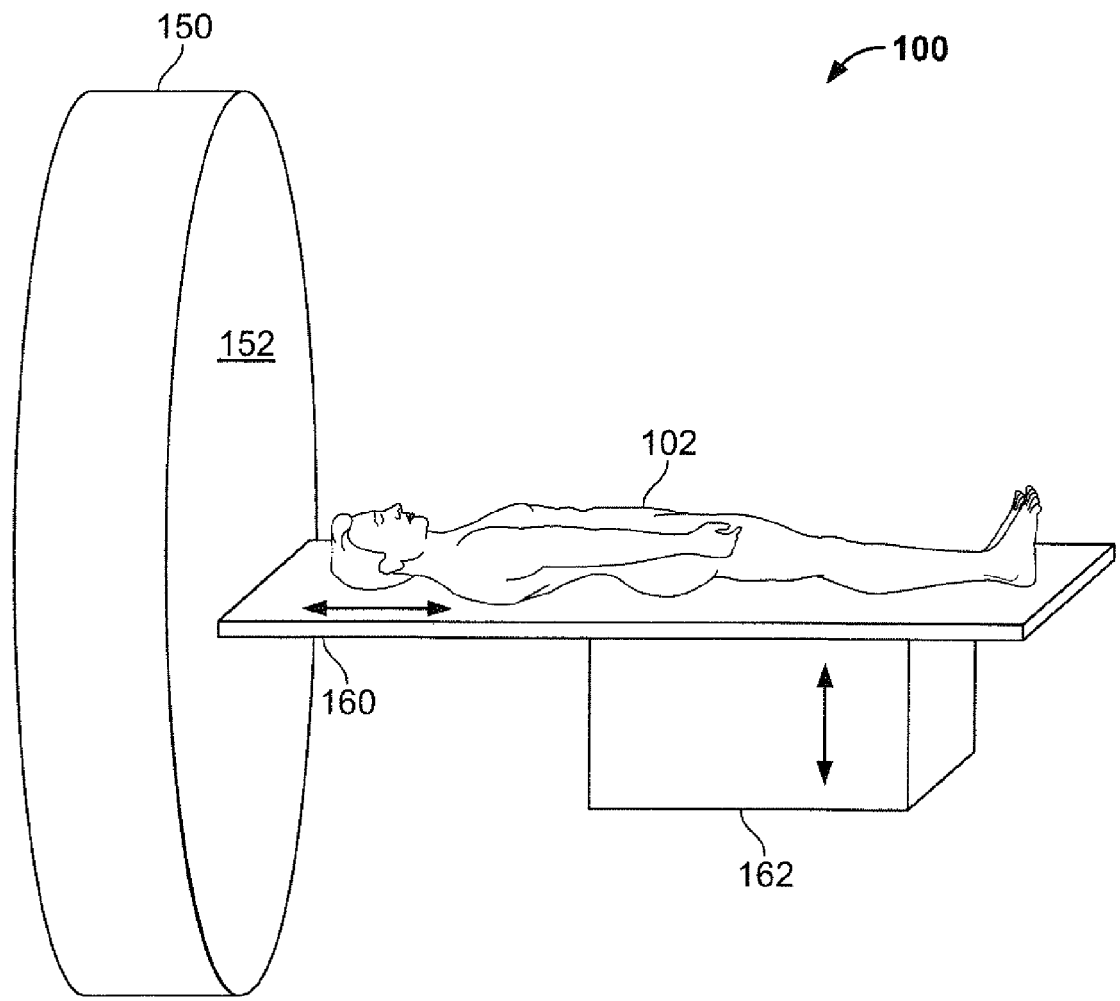
FIG. 1 is a diagram illustrating an imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for controlling the positioning of a plurality of imaging detectors. For example, in various embodiments, an imaging system having one or more Nuclear Medicine (NM) cameras having an array of heads that are individually and independently movable is provided. In some embodiments, one or more of the heads are capable of a plurality of types of movement, such as translation (e.g., radial translation across a circular cross-section of a bore configured to accept an object to be imaged), as well as rotation, pivoting, and/or swiveling of an individual detector head about an arm or other structure used to translate the detector head radially. The NM cameras in various embodiments are configured to acquire Single Photon Emission Computed Tomography (SPECT) data. The detectors, for example, may be Cadmium Zinc Telluride (CZT) detectors.

In some embodiments, the imaging detectors may be controlled to be positioned about an object to be imaged (e.g., a human patient). An imaging system may have a generally radial geometry consisting of an array of uniform distributed detector heads assembled or distributed around a gantry bore. Each detector head may have its own radial motion toward (or away) from the center of the gantry. A patient to be scanned lies on a table and transported to a scan area within the gantry bore. In some embodiments, the system utilizes an optimal or improved positioning algorithm or scheme for position the detectors of a radial multi-head CZT GP camera. The algorithm or scheme may provide for an optimal or improved approach of each detector head toward the patient body to provide ideal or improved proximity to an organ to be scanned, while preventing collisions between detectors heads as the heads radially approach the patient body. In some embodiment, once the detector heads are positioned around the patient body, the algorithm or scheme may provide for the activation (or deactivation) of individual detectors based upon final position reached with respect to the patient. The algorithm or scheme for positioning in various embodiments is based on defining strategic stop positions of the detectors during the radial motion toward the patient body regardless of patient body shape. For example, one or more rings at which certain detectors are stopped or inhibited from further radial advancement may be employed.

Further, the detector heads may be prevented from impacting or colliding with a patient and/or patient support structure (e.g., table or bed) by an Automatic Body Contouring (ABC) sub-system. The ABC sub-system may employ proximity sensors that detect the proximity of associated corresponding detector heads to a patient, bed or other obstacle. Additionally or alternatively, the 3D shape of the patient and/or support structure may be known from a measurement system such as Computed Tomography (CT) scan or 3D optical camera, among others. A patient safety device or pressure sensor device may be employed (using the proximity sensors and/or additional sensors) to prevent contact and/or injury to patients from approaching detector heads. In some embodiments, the imaging system may be configured to automatically retract a detector head a predetermined distance after it is sensed or determined that the detector head has contacted a patient or is within a threshold distance of the patient (e.g., due to patient movement after positioning of the detectors). In some embodiments, the detector heads may be radially advanced after a patient is introduced into a scanning area of the bore, while in other embodiments, the detector heads may be advanced radially inwardly before a patient is introduced into the bore. For example, the detector heads may be advanced as far inwardly as the detector heads may be consistent with the positioning algorithm or scheme, and then translated radially outwardly sufficiently to allow the patient to be advanced into the scanning area of the bore.

Various embodiments provide improved imaging. For example, the time for positioning detectors of a system may be reduced. As another example, improved placement of detectors (e.g., closer to an object to be imaged) may be achieved. As one more example, patient comfort may be increased and/or patient anxiety reduced. As another example, system downtime (e.g., downtime for positioning detectors) may be reduced. As one more example, collisions between detectors may be reduced and/or avoided.

FIG. 1 illustrates an imaging system 100 in accordance with an embodiment. As seen in FIG. 1, the depicted imaging system 100 includes a gantry 150 with a bore 152 therethrough. The gantry 150 may have coupled thereto imaging detectors (see, e.g., FIG. 2 and related discussion). The imaging system 100 may be utilized to image a subject 102. In the embodiment depicted in FIG. 1, the subject 102 is positioned on a patient table 160 that includes a support 162 (e.g., a patient table or bed mechanism) that allows movement of the patient table 160 as described herein. For example, the subject 102 may be moved upwards/downwards or left/right (along the examination axis) as viewed in FIG. 1. Thus, the subject 102 may be moved through the bore 152 (e.g., to and from a scanning area of the bore) and imaged, using one or more of the detector configurations described herein. In the illustrated embodiment, the system 100 moves the subject 102 along the examination axis.

Figure 2:
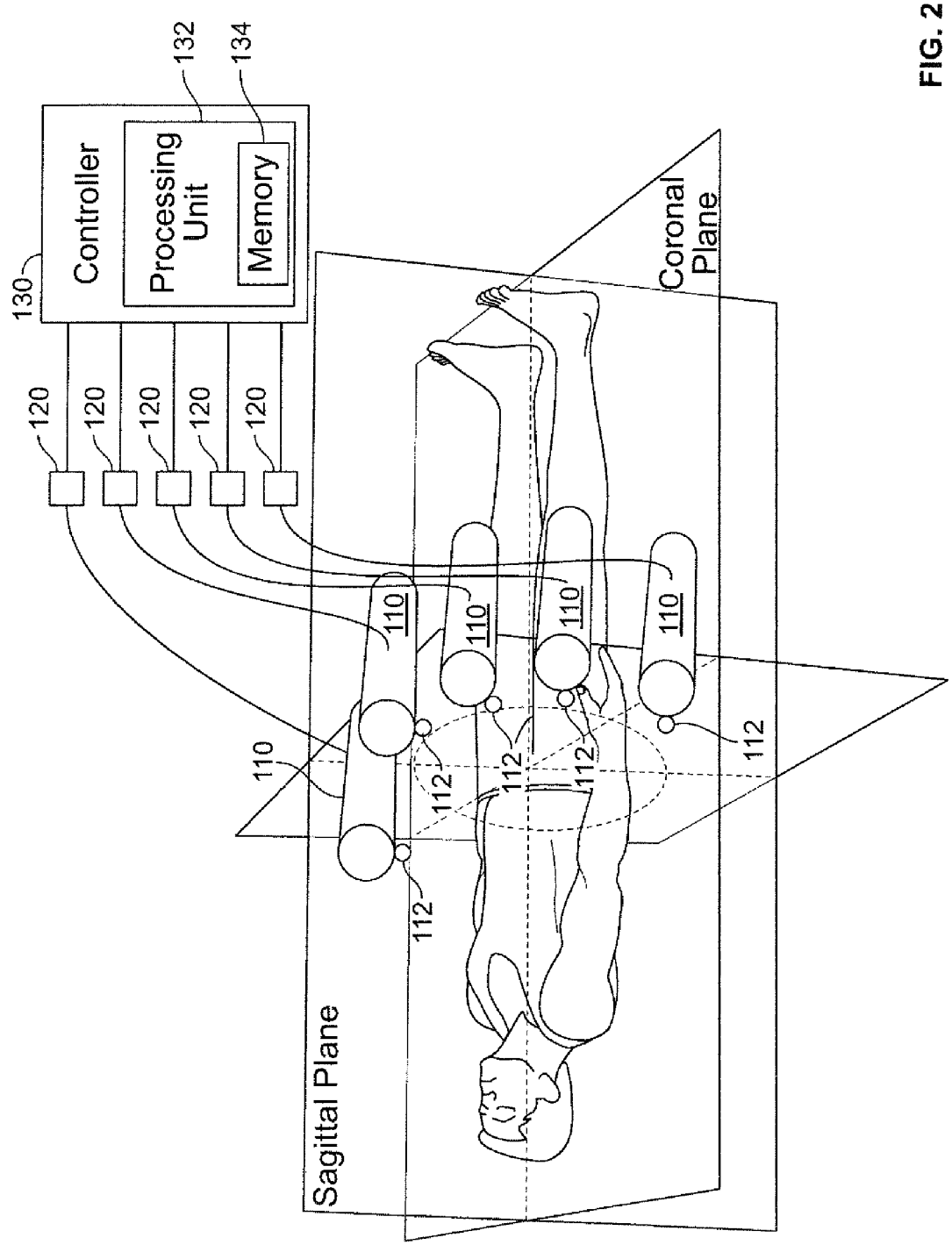
FIG. 2 provides a schematic perspective view of the imaging system of FIG. 1 with a subject positioned within a bore for scanning in accordance with an embodiment.

FIG. 2 provides a schematic perspective view of the imaging system 100 with a subject 102 (e.g., a human patient) positioned within the bore 152 for scanning. As seen in FIG. 2, the imaging system includes imaging detector units 110 that are positioned around at least a portion of the subject 102 (in some embodiments spaces partially or entirely around the subject 102). For simplicity and ease of description, only 5 detector units are shown, however additional detector units 110 may be employed. For simplicity and ease of description, additional components or aspects such as the bore 152 and patient table 160 are also omitted from FIG. 2.

The depicted imaging system 100 includes the detector units 110 as well as corresponding actuators 120 for the detector units 110, and a controller 130. Generally, the controller 130 controls the actuators 120 to position the detector units 110 for scanning. The controller 130 may utilize a positioning algorithm or scheme as described herein to determine the positions of the various detector units 110 during scanning, and to position the detector units 110. The detector units 110 are configured to collect imaging information. For example, each detector unit 110 may include a CZT detector configured to collect nuclear medicine imaging information during a scan. Each detector unit 110 may also include a collimator configured for use with the CZT detector.

Figure 3:
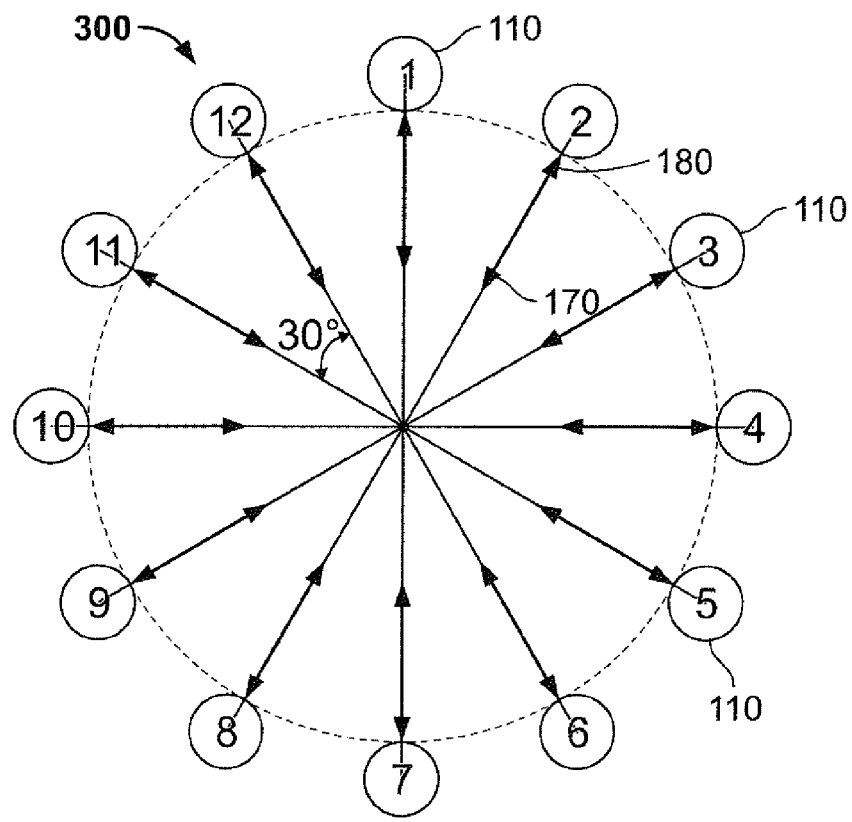
FIGS. 3 and 4 are diagrams illustrating motion of detectors in accordance with an embodiment.
Figure 4:
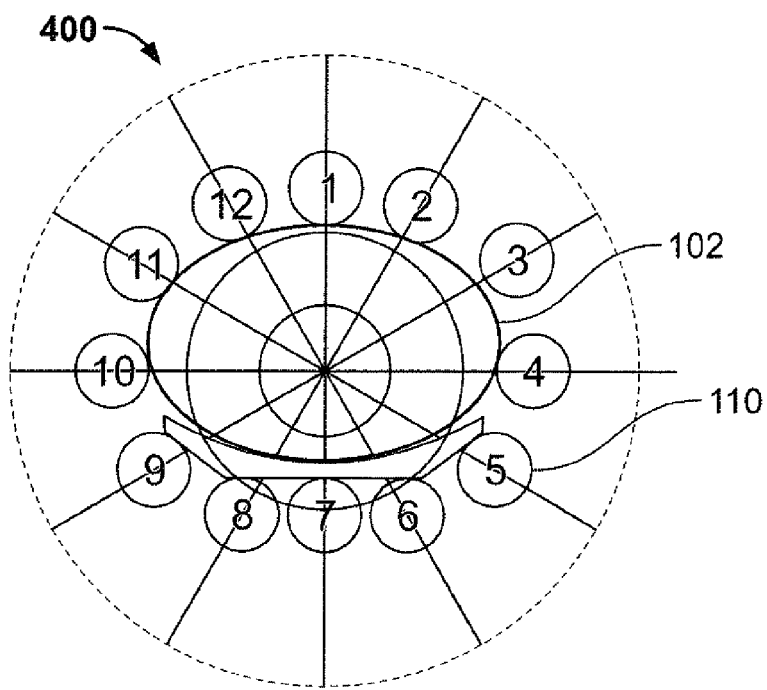

The detector units 110 are distributed about the bore 152, and are radially articulable within the bore (e.g., the detector units may be translated radially toward or away from the center of the bore. For example, FIGS. 3 and 4 illustrate radially positionable detector units 110 at an exterior position 300 (e.g., the detector units at a maximum position radially away from the center of the bore 152) in FIG. 3, and with the detector units at an interior (e.g., imaging) position 400 in FIG. 4. In FIG. 4, the interior position corresponds to an imaging position. Additionally or alternatively, interior positions may include an initial position at which at least some of the detector units 110 are disposed radially inwardly of the imaging position (e.g., imaging position shown in FIG. 4). The detector units 110 may be initially positioned at such an initial position before introduction of the subject 102 into the scanning area of the bore 152, with the detector units 110 moved radially outwardly to accept the subject 102, in contrast to embodiments which may begin at the exterior position 300 shown in FIG. 3, in which the detector units 110 may be moved radially inwardly after the subject 102 is introduced to the bore or during introduction of the subject 102 into the bore 152. For example, some patients may find the radially inward movement of the detector units 110 to cause feelings of claustrophobia or other discomfort, and the detector units 110 may be initially positioned more radially inward and subsequently translated radially outwardly to alleviate such discomfort.

As seen in the embodiment depicted in FIGS. 3 and 4, the detector units 110 are positioned and spaced evenly, such as distributed along a gantry (e.g., the gantry 150) evenly along the circumference of the gantry. For example, 12 detector units 110 (individually labelled "1," "2", "3" . . . "12") are depicted in FIG. 3, with the detector units 110 shown as spaced apart by 15 degrees. Other numbers of detector units and/or spacings may be utilized in alternate embodiments. For example, an uneven spacing and/or additional or fewer detectors 102 may be provided. As can be seen, the detector units 110 are movable radially inward along direction 170 from the exterior position shown in FIG. 3 to position the detector units 110 adjacent or near to the subject 102 for imaging in the interior or imaging position shown in FIG. 4. Similarly, the detector units 110 are movable radially outward along direction 180 from the imaging position shown in FIG. 4 to the exterior position shown in FIG. 3. Additionally or alternatively, one or more detector units may be stopped at an intermediate position between an exterior position and an imaging position adjacent or near to the subject 102, for example at a safe or stop ring position as described herein (see, e.g., FIGS. 5-8 and related discussion). It may be noted that the individual detector units 110 are movable different distances (e.g., one or more detector units 110 may be moved different distances than one or more other detector units 110) depending on the size, shape, etc., of the subject 102.

Returning to FIG. 2, the detector units 110 each include a corresponding proximity sensing device 112. The proximity sensing device 112 may be used to sense or determine when a given detector unit 110 is within a predetermined threshold distance of the subject 102 beyond which the detector unit 110 may be considered in contact with or otherwise too close to the subject 102. The proximity sensing device 112 may be used to position a corresponding detector unit 110 at a desired distance from the subject 102. In various embodiments, the proximity sensing device 112 may include more than one detector or sensor, and may include more than one type of detector or sensor.

In the illustrated embodiment, each detector unit 110 has an actuator 120 associated therewith. For example, each actuator 120 may be configured as an arm to radially translate a corresponding detector unit 110 toward and away from a center of the bore 152. The actuators 120 may be operably coupled to and controlled by the controller 130. It may be noted that each detector unit 110 may be pivotable about an axis (e.g. an axis passing through the actuator 120 and/or the detector unit 110) to position the detector unit 110 during scanning. For example, a detector unit 110, after being radially advanced close to the subject 102, may be pivoted to have a portion facing a portion of the subject 102 to be scanned. Additionally or alternatively, the detector unit 110 may be pivoted to be swept over a range during imaging data collection. In some embodiments, the detector unit 110 may include one or more imaging modules that may be pivoted within the detector unit 110. For additional discussion regarding actuators and/or arms for positioning the detector units in various embodiments, see FIGS. 9-11.

Returning to FIG. 2, the controller 130 is configured to control movement of detector units 110. For example, the controller 130 may position the detector units 110 pursuant to a positioning algorithm or scheme as discussed herein. The controller 130 may also be utilized to adjust the position of one or more detectors. For example, after the detector units 110 are positioned, the subject 102 may move and contact or come within a threshold distance of a particular detector unit 110. Responsive to information provided by the proximity sensing device 112 of the particular detector unit 110 indicating the contact or proximity, the controller 130 may adjust the particular detector unit 110. For example, the controller 130 may retract the particular detector unit 110 a predetermined retraction distance to provide a desired space or distance between the detector unit 110 and the subject 102. In the illustrated embodiment, the controller 130 includes a processing unit 132 and a memory 134. The processing unit 132 may include processing circuitry configured or adapted to perform various actions (e.g., to implement a positioning algorithm or scheme as described herein).

Generally, the controller 130 is operably coupled to the detector units 110 and configured to control the positioning of the detector units 110. The controller 130 in various embodiments is configured to position an external group of the detector units 110 at predetermined intermediate portion corresponding to a ring (see, e.g., examples discussed below in connection with FIGS. 5-8), with the ring having a radius corresponding to the total number of detector units 110, and the size of the detector units. Generally speaking, the larger the number of detector units 110 (and/or the larger the size of the detector units), the larger the radius will be. The controller 130 may also be configured to position an internal group of the detector units 110 radially inside the ring.

In some embodiments, the controller 130 may be configured to position different groups of detector units 110 at corresponding plural intermediate positions (e.g., a first group at a first ring, a second group at a second ring). Each intermediate position may be configured to accommodate twice as many detector units 110 as an internally adjacent position (e.g., 3 detector units at a second ring and 6 detector units at a first ring disposed adjacent to and radially outward of the second ring).

In various embodiments, the ring of the intermediate position may correspond to a radial position at which the detector units 110 contact each other. For example, a safe or stop ring at which a group of detector units are positioned (e.g., the centers of the detector units are at the radial position defined by the ring) may be larger than the radius at which all detector units would contact each other by a predetermined offset (see, e.g., FIG. 5b and related discussion).

Additionally or alternatively, in various embodiments, the controller 130 may be configured to position the detector units 110 from an initial position at which at least some of the detector units 110 are disposed internally of the ring of the intermediate position. In other embodiments, the controller 130 may be configured to position the detector units 110 from an initial position at which each of the detector units are disposed externally of the ring of the intermediate position. Further, in some embodiments, the controller 130 may advance each of the detector units 110 simultaneously from the initial position to the intermediate position.

As indicated above, the controller 130 may be configured to utilize a positioning algorithm or scheme. In various embodiments, the positioning algorithm may be based upon defining one or more strategic stop positions (e.g., rings, with each ring defined by a radius extending from the center of the bore 152) during the radial motion of the detector units 110 toward the subject 102, regardless of the size or shape 102 of the subject. Different groups of detector units 110 are assigned to different stop positions (e.g., rings), with each detector unit 110 stopping at the ring assigned to the particular detector unit 110, unless the detector unit 110 has already stopped moving inwardly radially due to proximity with the subject 102.

For example, in some embodiments, each detector unit 110 may be substantially similar such that it may be assumed that all detector units 110 have the same radial range, and have the same outer-most and inner-most positions at similar radial positions referenced to the center of the bore 152.

FIGS. 5a and 5b illustrates various rings or stop positions of the detector units 110 in various embodiments. The following definitions and assumptions are utilized in connection with FIGS. 5a and 5b and additional examples discussed herein. Each detector (e.g., detector unit 110) will be individually referred to as Detector "n," where "n"=1, 2, . . . N, with N being the total number of detectors. The particular algorithms or schemes discussed herein are most appropriate for use with systems where N=6, 12, 24, 48, 96, and so on. Detector 1 is shown at a top position (e.g., corresponding to 12:00 on a clock face), with the remaining detectors numbered sequentially clock-wise. The radii (n) shall refer to the radial position (distance from center) of Detector n. The radial position of a given detector may be determined by the location of the center of the detector. Inward radial motion shall refer to radial motion toward the center of the bore 152, and outward radial motion shall refer to radial motion away from the center of the bore 152. Each detector is assumed to have a circular shape with a radius r. Further, each detector is equipped with a sensor that signals when the detector almost touches the patient body. The signal is referred to herein as BC(n) (e.g., body contour for Detector (n)), where BC(n)=1 when the sensor for Detector (n) is activated due to proximity with the subject 102.

An initial ring (e.g., "Ring 1" or "first ring") is the outer-most ring. Ring 1 is the radial position where each detector (n=1, 2 . . . N) would contact adjacent detectors if at the same distance from the center of the bore 152 (e.g., each detector started moving inward at the same time and at the same speed from a common outermost radial limit position).

A second ring (e.g., "Ring 2" or "second ring") is the next outermost ring, and is disposed radially inwardly of Ring 1. Ring 2 is the radial position where detectors numbered n=(1+2k), where k=0, 1, 2, 3 . . . (N−2)/2, would contact adjacent detectors if at the same distance from the center of the bore 152 (e.g., each detector started moving inward at the same time and at the same speed from a common initial radial position, such as Ring 1). For a system having 24 detectors, Ring 2 would correspond to the radial position of contact for Detectors 1, 3, 5, 7, 9, 11, 13, 15, 17, 19, 21, and 23 (e.g., the odd-numbered detectors, or every other detector starting with Detector 1).

A third ring (e.g., "Ring 3" or "third ring") is the next outermost ring, and is disposed radially inwardly of Ring 2, such that Ring 2 is interposed between Ring 1 and Ring 3. Ring 3 is the radial position where detectors numbered n=(1+4k), where k=0, 1, 2, 3 . . . (N−4)/4, would contact adjacent detectors if at the same distance from the center of the bore 152 (e.g., each detector started moving inward at the same time and at the same speed from a common initial radial position, such as Ring 2). For a system having 24 detectors, Ring 3 would correspond to the radial position of contact for Detectors 1, 5, 9, 13, 17, and 21) (e.g., every fourth detector starting with Detector 1).

A fourth ring (e.g., "Ring 4" or "fourth ring") is the next outermost ring, and is disposed radially inwardly of Ring 3, such that Ring 3 is interposed between Ring 2 and Ring 4. Ring 4 is the radial position where detectors numbered n=(1+8k), where k=0, 1, 2, 3 . . . (N−8)/8, would contact adjacent detectors if at the same distance from the center of the bore 152 (e.g., each detector started moving inward at the same time and at the same speed from a common initial radial position, such as Ring 3). For a system having 24 detectors, Ring 4 would correspond to the radial position of contact for Detectors 1, 9, and 17 (e.g., every eighth detector starting with Detector 1). Thus, for a system having 24 detectors, a first group of detectors (e.g., Detectors 2, 4, 6, 8, 10, 12, 14, 16, 18, 20, 22, and 24) may be stopped or inhibited from further radial advancement than the first ring, with the remaining detectors advancing. Further, a second group of detectors (e.g., Detectors 3, 7, 11, 15, 19, and 23) may be stopped or inhibited from further radial advancement than the second ring, with the remaining detectors advancing. Further still, a third group of detectors (e.g., Detectors 5, 13, and 21) may be stopped or inhibited from further radial advancement than the third ring.

For detector systems having more than 24 detectors, additional rings may be added. Generally, for a system where N=6, 12, 24, 48, 96, and so on, various rings may be defined as the radial positions number n=(1+2λ) where k=0, 1, 2, 3, . . . (N−λ/λ), where λ=2, 4, 8, 16, 32, 64, and so on.

FIG. 5a illustrates three rings for a system having 12 detectors (e.g., N=12), for example as seen in FIGS. 3 and 4. In various example embodiments, the ring of contact (e.g., a position at which all detector units, or all remaining detector units not stopped at a radially outward position, come into contact with each other) may be determined as follows. For Ring 1 (the first ring 510), the radius of Ring 1 (RR1)=(r*(N−π))/π. For Ring 2 (the second ring 520), the radius of Ring 2 (RR2)=(r*(N/2−π)/π. In general, the radii of Ring(ρ) for N−6, 12, 24, 48, 92 . . . , if (N/2$^ρ$)>3, is given by (r*[N/2$^ρ$−π])/π. If (N/2$^ρ$)=3, the radii of the last ring is given by (1.5)*r. Thus, for the various rings (e.g., the first ring 510, the second ring 520, the third ring 530), the radius of a ring corresponds to the number of detector units (N) as well as the size of the detector units (e.g., r). As shown in FIG. 5, the first ring 510 corresponds to the position of all detectors in contact with each other. Detectors 1, 3, 5, 7, 9, and 11 are allowed to advance past the first ring 510, and the second ring 520 corresponds to the position of Detectors 1, 3, 5, 7, 9, and 11 in contact with each other. Similarly, Detectors 1, 5, and 9 are allowed to advance past the second ring 520, and the third ring 530 corresponds to the position of Detectors 1, 5, and 9 in contact with each other.

It may be noted after one group of detectors has advanced past a stopping ring or intermediate position, one or more of the detectors previously stopped at a stopping ring or intermediate position may be advanced radially inwardly, if appropriate clearance from already advanced detectors is available. The specific numbers of detectors may be adjusted from the examples discussed herein, using positioning algorithms or schemes employing general principles discussed herein with appropriate adjustments for determining the stopping positions and groupings of detectors based on the total number of detectors.

It may be noted that the rings in FIG. 5a are defined by the points of contact between various detectors. In some embodiments, the ring used to define one or more intermediate positions may be defined by the radius for the ring defined by contact plus a radial offset. The radial offset provides an increment to prevent collisions during positioning of the detectors. FIG. 5b illustrates a safe ring in accordance with various embodiments. For example, in FIG. 5b, the first ring 510 of FIG. 5a is shown, with a first safe ring 610 having a radius that is greater by offset 612 than the radius of the first ring 510. Thus, the first safe ring 610 corresponds to the first ring 510 by having a radius that is a predetermined distance greater than the radius of the first ring 510. Further, each ring of contact (e.g., the first ring 510, the second ring 520, and the third ring 530) for a given system may have a corresponding safe ring that defines a stopping point for a group of detectors. For example, in FIG. 5b, the Detectors 2, 4, 6, 8, 10, and 12 may be controlled by the controller 130 to stop no closer to the center of the bore then when the detectors arrive at the first safe ring 610 (e.g., when the centers of the detectors are at the radius defined by the first safe ring). (One or more detectors may be stopped at a greater radial distance greater than a ring assigned to the detectors, for example based on a signal from a proximity sensor indicating that a given detector is close to contacting the subject being imaged.) For example, for a system with 12 detectors arranged as shown in FIGS. 5a and 5b, with each detector head about 50 millimeters, a safe ring may be defined as having a radius about 8.5 millimeters greater than a corresponding ring of contact. Detectors assigned to stop at the given ring may be stopped at the safe ring, with remaining detectors allowed to proceed. After the remaining detectors proceed, in some embodiments, one or more of the detectors assigned to stop at the given ring may be allowed to advance after the remaining detectors are clear.

Thus, the positioning algorithm or scheme allows for a given detector to be advanced until 1 of 2 conditions is satisfied. The detector is prevented from further radial advancement if either (1) BC(n) for the detector is 1 (the detector is within a predetermined distance of the object to be imaged or a support structure), or (2) the detector has reached a designated stopping point (e.g., a safe ring) with which the detector has been associated. For example, the safe ring for a given detector in various embodiments may be identified in the following table, where n=the detector's identifying number, and ρ is the safe ring.

| n | ρ |
|---|---|
| (2k) for k = 0, 1, 2, 3, . . . N/2 | 1 |
| (3 + 4k) for k = 0, 1, 2, 3, . . . (N − 4)/4 | 2 |
| (5 + 8k) for k = 0, 1, 2, 3, . . . (N − 8)/8 | 3 |

-continued

| n | ρ |
|---|---|
| (9 + 16k) for k = 0, 1, 2, 3, . . . (N − 16)/16 | 4 |
| . . . | |

For example, for N=12 or N=24, the following table describes the stop rings assigned to various detectors in accordance with some embodiments:

| N = 12 | N = 24 | Stop Ring |
|---|---|---|
| 2, 4, 6, 8, 10, 12 | 2, 4, 6, 8, 10, 12, 14, 16, 18, 20, 22, 24 | 1 |
| 3, 7, 11 | 3, 7, 11, 15, 19, 23 | 2 |
| 1, 5, 9 | 5, 13, 21 | 3 |
| N/A | 1, 9, 17 | 4 |

Thus, when N=12, Detectors 2, 4, 6, 8, 10, and 12 do not advance past the first stop or safe ring, Detectors 3, 7, and 11 do not advance past the second stop or safe ring, and Detectors 1, 5, and 9 do not advance past the third stop or safe ring. Thus, for example, the first ring may be understood as an intermediate position, with one or more of the even numbered detectors forming a group that is positioned at the intermediate position (some detectors may be positioned radially outward of the intermediate position due to proximity with an object or structure), and one or more of the odd numbered detectors forming a group that may be positioned radially inside the intermediate position or ring (again, some detectors may be positioned radially outward of the intermediate position due to proximity with an object or structure). Also, the second ring may be understood as an intermediate position with Detectors 3, 7, and 11 forming a group that is positioned at the intermediate position, and Detectors 1, 5, and 9 forming a group that is positioned radially inside the intermediate position or ring (assuming the detectors have not contacted or approached within a threshold distance of the object to be imaged).

When N=24, Detectors 2, 4, 6, 8, 10, 12, 14, 16, 18, 20, 22, 24 do not advance past the first stop or safe ring, Detectors 3, 7, 11, 15, 19, 23 do not advance past the second stop or safe ring, Detectors 5, 13, 21 do not advance past the third stop or safe ring, and Detectors 1, 9, 17 do not advance past the fourth stop or safe ring. It may be noted that some, none, or all of the detectors determined or identified as permitted to advance past a given ring may advance past the ring. For example, if one group has approached the object being imaged within a threshold distance before approaching the ring, the group may be prevented from reaching the ring, while another group that has not approached the object within a threshold distance may advance to and past the ring. As indicated by the above examples, one or more intermediate positions or stop rings may be configured to accommodate twice as many detector units as an internally adjacent position. In various embodiments, detectors can be advanced as a group and/or individually.

Figure 6:
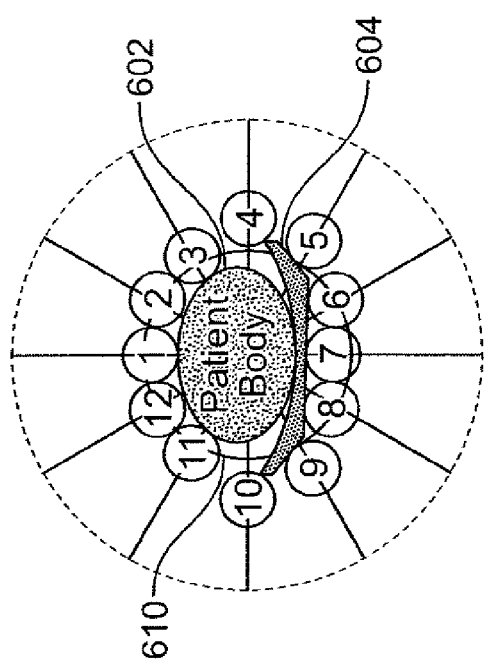
FIG. 6 is a diagram illustrating the positioning of detector units in accordance with an embodiment.
Figure 8:
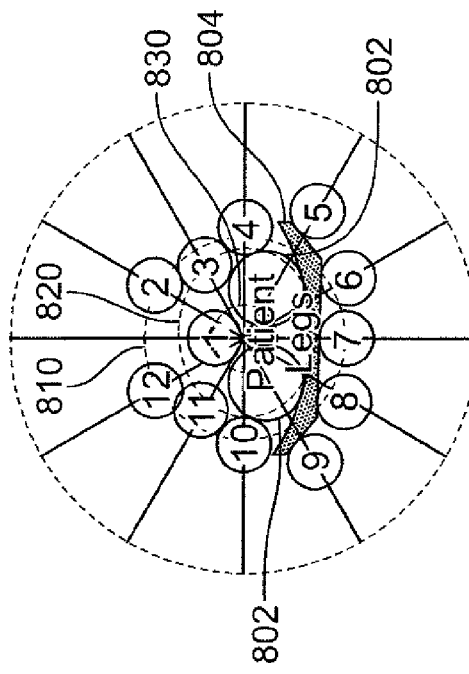
FIG. 8 is a diagram illustrating the positioning of detector units in accordance with an embodiment.
Figure 7:
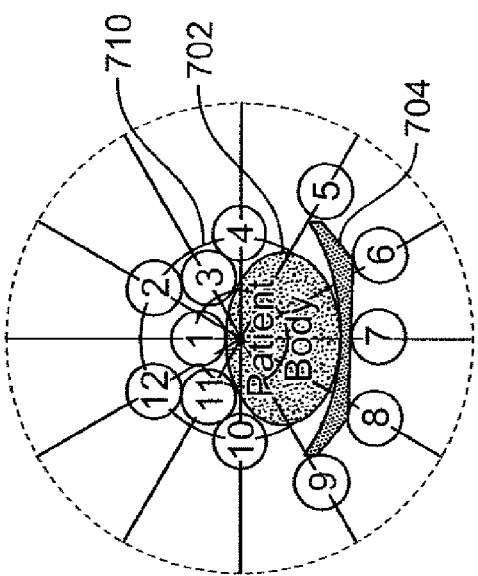
FIG. 7 is a diagram illustrating the positioning of detector units in accordance with an embodiment.

FIGS. 6, 7 and 8, as well as FIG. 4, show examples of detectors positioned for imaging a patient body. In the examples of FIGS. 6-8, the detectors are arranged in groups of 12 and numbered from 1-12 (as in FIGS. 5a and 5b), with even numbered detectors associated with a first stop ring (e.g., prevented or inhibited from advancing radially inward past the first stop ring), detectors 3, 7, and 11 associated with a second stop ring, and detectors 1, 5, and 9 associated with a third stop ring. It may be noted that other numbering schemes or associations of particular detectors to particular stop rings may be employed in alternate embodiments.

The example of FIG. 4 may be understood as an example where each detector has reached proximity to the patient body before reaching a stop ring. In the example of FIG. 6, Detectors 4-11 have stopped advancing radially inwardly before reaching a stop ring 610 due to proximity to either a patient body 602 or a structure 604 (e.g., bed). Detectors 2 and 12 are stopped from further radially inward advancement by a positioning algorithm or algorithm in accordance with various embodiments at the stop ring 610, and Detectors 1 and 3 in FIG. 6 have been advanced past the stop ring 610 to a point of proximity with patient body 602 for scanning.

In the example depicted in FIG. 7, Detectors 5-9 and 10 are stopped from further advancement radially inward due to proximity with a patient body 702 or structure 704 before reaching a stop ring 710. Detectors 2, 4, and 12 are stopped at the stop ring 710. Detectors 1, 3, and 11 are prevented from advancing further inwardly by proximity with patient body 702 after passing the stop ring 710. In various embodiments, all or some detectors that have been stopped at a stop ring (e.g., stop ring 710) may be idle during scanning, or not used to collect scanning information. For example, in the example illustrated in FIG. 7, Detectors 2 and 12 may be idle during scanning.

In the example shown in FIG. 8, in which the legs of a patient are to be imaged, Detectors 4-9 are prevented from further radially inward advancement due to proximity with a patient body 802 or structure 804. Also, detectors 2, 10 and 12 are stopped at a first stop ring 810, while detectors 3 and 11 are stopped at a second stop ring 820 pursuant to a positioning scheme in accordance with various embodiments. Detector 1 advances, pursuant to the positioning scheme, past the second stop ring 820 and stops at a third stop ring 830, with detector 1 positioned between the legs of the patient.

Generally, for embodiments with 12 detectors as discussed above, at any stage, any detector that reaches the patient or a support structure (or a threshold distance near the patient or a support structure) will be prevented or inhibited from further movement radially inwardly. At a first stage, all detectors (Detectors 1, 2, 3, 4, 5, 6, 7, 8, 9, 10, 11, and 12) will move inwardly. Detectors 2, 4, 6, 8, 10, 12 will stop at a first ring even if not yet in proximity to the patient or a support structure. At a second stage, Detectors 1, 3, 5, 7, 9, and 11 will be advanced inwardly. Detectors 3, 7, and 11 will stop at a second ring, even if not proximate to the patient or a support structure. At a third stage, Detectors 1, 5, and 9 will advance toward a third ring, stopping at the third ring if not already stopped due to proximity with the patient or a support structure. In some embodiments, one or more detectors stopped at a given ring may be advanced past the given ring after other detectors have advanced sufficiently to provide a clearance. In some embodiments, for example with a known shape of patient and/or support structure, detectors known to be idle during information acquisition may be prevented from advancing.

It may be noted that the object to be imaged may or may not be centered within the bore in various embodiments. For example, the height of the patient table (e.g., patient table 160) may be adjustable along a vertical axis (e.g., up and down as seen in FIG. 6) and/or along a lateral axis (e.g., to the left or right as seen in FIG. 6). Thus, a patient may be moved along an axial direction (e.g., into the bore) to bring a desired section of the patient into the field of view (FOV) of the camera, with vertical and/or lateral motion used for centering the patient within the camera. Further, in some embodiments, the table height (and/or lateral position of the table) may be adjusted to provide improved positioning of the detectors relative to the patient, with the patient not centered within the bore. For example, the contour of the body of the patient may be known prior to positioning the camera heads (e.g., from a CT scan done prior to the NM imaging, or using other techniques such as optical profiling). The table height may then be selected and set such that the detectors may approach the body upper side such that the detectors are proximate the body before the possibility of collision (an example of an approach where the detectors are proximate before a possibility of collision may be seen in FIG. 4; an approach where the detectors have the possibility of colliding before the detectors are proximate the body may be seen in FIG. 7.). In such an example, elevating the table (and/or adjusting the table laterally) allows more detectors to be near the body, thus increasing the total sensitivity of the camera, and enables collecting data from more views at the time.

In some organ-specific imaging, such as cardiac imaging, an optimal or improved positioning of the detector may be provided by a configuration in which the detectors are closely positioned in proximity to the desired organ (e.g., heart), while the positioning of the detectors far from the heart (e.g. near the back) contribute to the image quality relatively weakly. By using both lateral and vertical positioning of the bed, optionally placing the patient in non-centric location vs. the center of the gantry, a better image may be obtained by positioning the organ of interest in proximity to a relatively large number of detectors.

Figure 9:
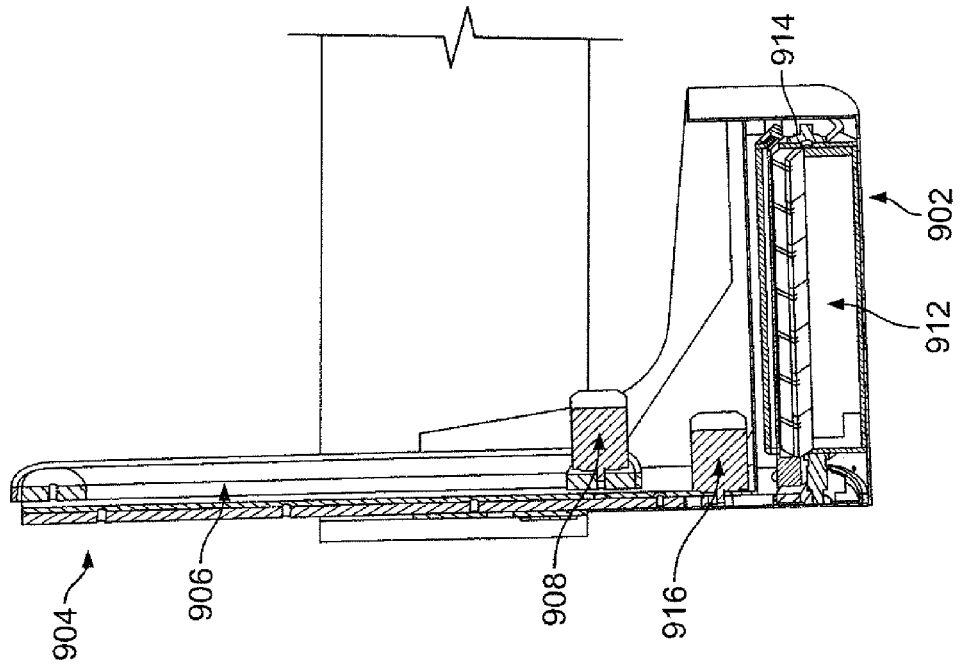
FIG. 9 is a diagram illustrating a detector arm configuration in accordance with an embodiment.
Figure 9:
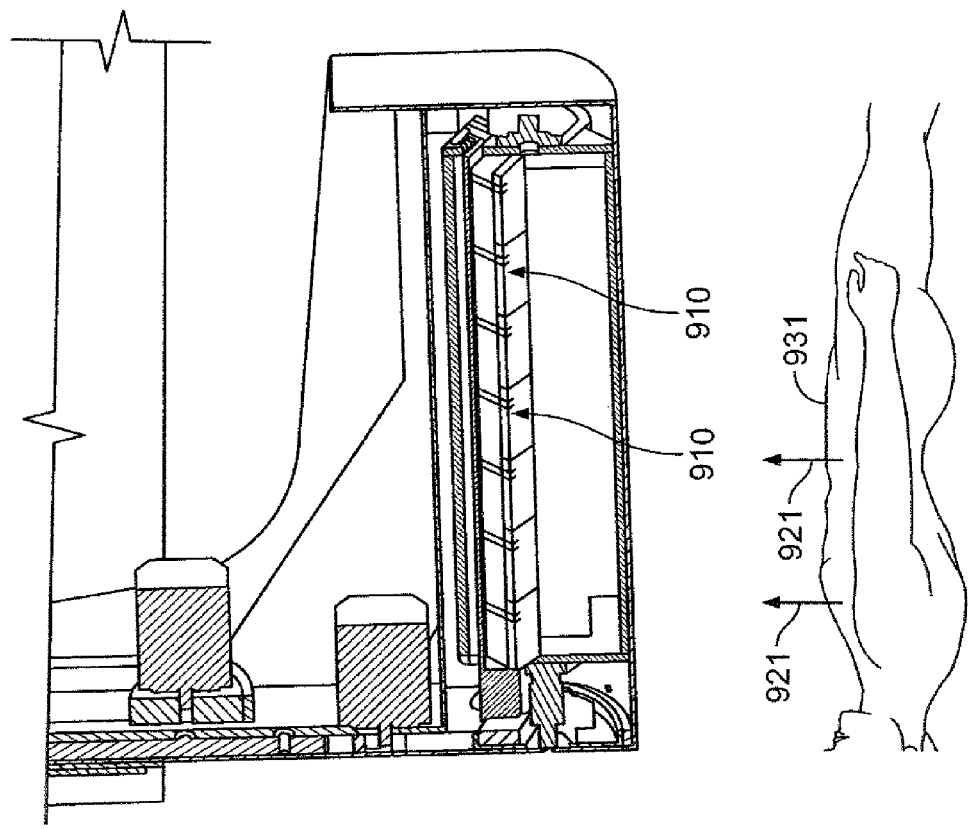
Figure 10:
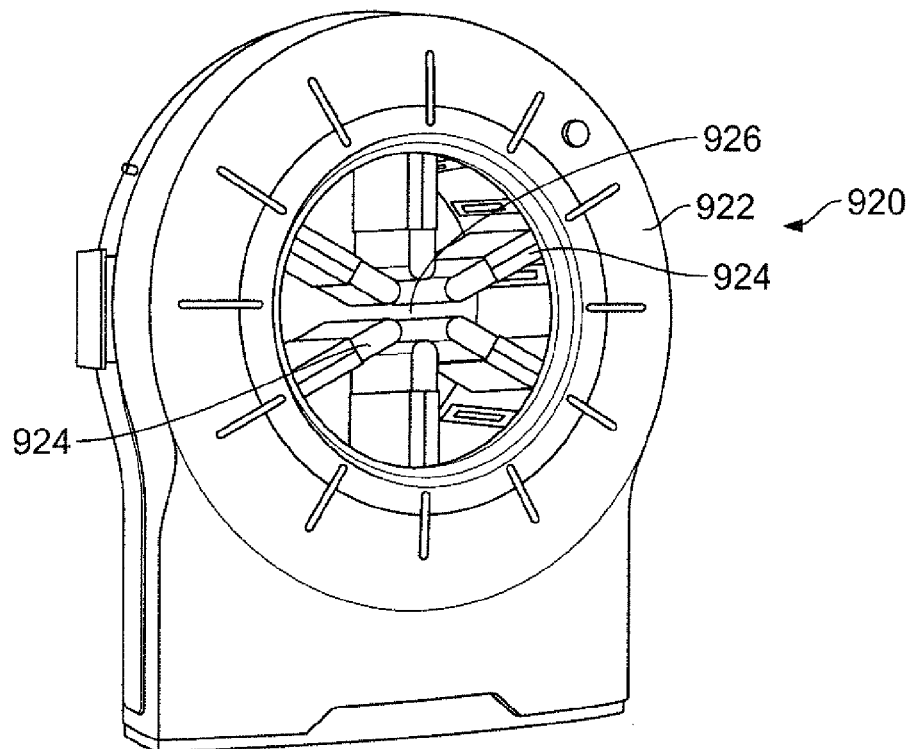
FIG. 10 is a perspective view of an imaging system in accordance with another embodiment.
Figure 11:
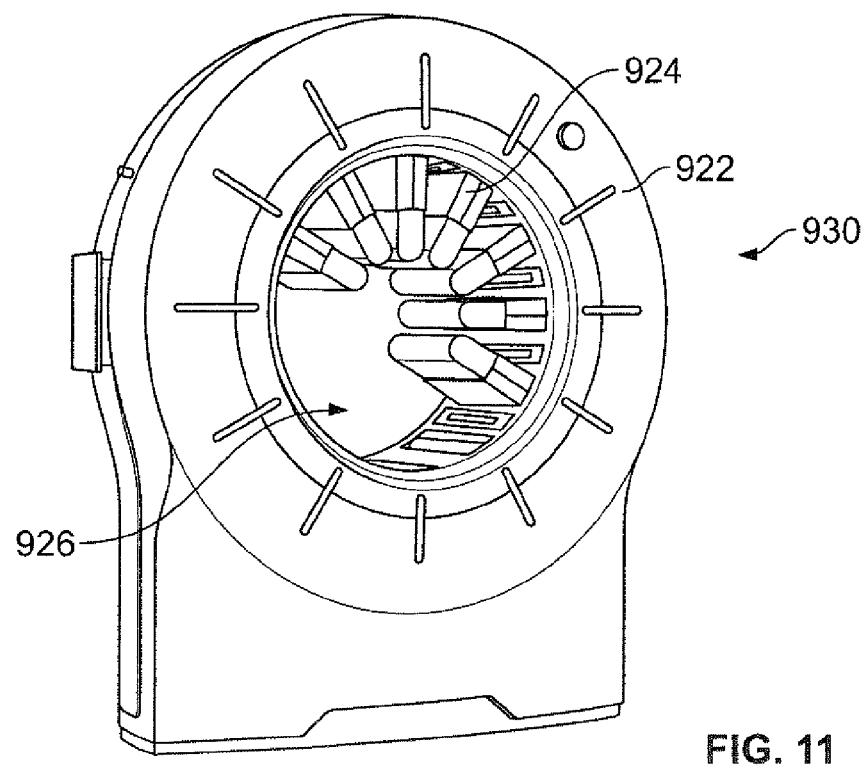
FIG. 11 is a perspective view of an imaging system in accordance with another embodiment.

FIGS. 9, 10, and 11 provide examples of supporting arms or structures in accordance with various embodiments. One arrangement 900 is shown in FIG. 9 illustrating an imaging detector configuration wherein a detector head 902 is mounted at one end of an arm 904 that includes a rail 906 to allow radial movement, such as shown between the positions shown in FIGS. 3 and 4. The imaging detector of FIG. 9 is positioned to receive gamma rays 921 from a patient 931. The movement may be controlled using a radial motion motor 908. The detector head 902 in the illustrated embodiment includes a plurality of imaging modules 910 (illustrated as CZT modules) that may be aligned in one or more rows (a single row is illustrated in the embodiment shown). As can be seen, a collimator 912 may be provided and coupled to one or more of the imaging modules 910. Additionally, the imaging modules 910 are coupled to a support 914 (e.g., a rod) that allows rotation or pivoting movement of the imaging modules 910 within the detector head 902. For example, a motor, such as a sweep motor 916 may be provided to control and move the imaging modules 910 to sweep across a region of interest (e.g., rotate or pivot a defined number of degrees).

Additionally, different configurations may be provided. For example, within a single cover or a single detector head, multiple detector units or modules may be provided. Additionally, one or more detectors may be fixed or mounted (or within) a patient table or a support portion thereof.

It should be noted that a plurality of arms supporting the detector units may be provided in different configurations. For example, as shown in FIG. 10, a system 920 may be provided with a gantry 922 having a plurality of arms 924 (e.g., movable supports) that extend and/or are movable radially inward and outward from the gantry 922. It should be noted that the arms 924 are spaced apart circumferentially around the entire bore 926 in this embodiment. It also should be noted that additional or fewer arms and different spacing between arms 924 may be provided. The arms 924 may be movable and may be embodied as the detector carriers 1316 (shown in FIG. 13 below) in some embodiments. Additionally, each arm 924 may support one or more detector units or modules. Other variations include arms 924 that are provided along only a portion of the circumference of the bore 926 as illustrated in the system 930 of FIG. 11. It should be noted that although the arms 924 are illustrated along about 180 degrees, the arms 924 may be provided along more or less of the bore 926, such as more or less than 180 degrees. It should be noted that for the configuration shown in FIG. 11, rotations greater than 180 degrees may be used to provide imaging in both prone and supine positions of the subject. For example, in some embodiments, rotation of about 210 degrees is provided. However, the rotation may be more or less than 210 degrees as desired or needed.

Figure 12:
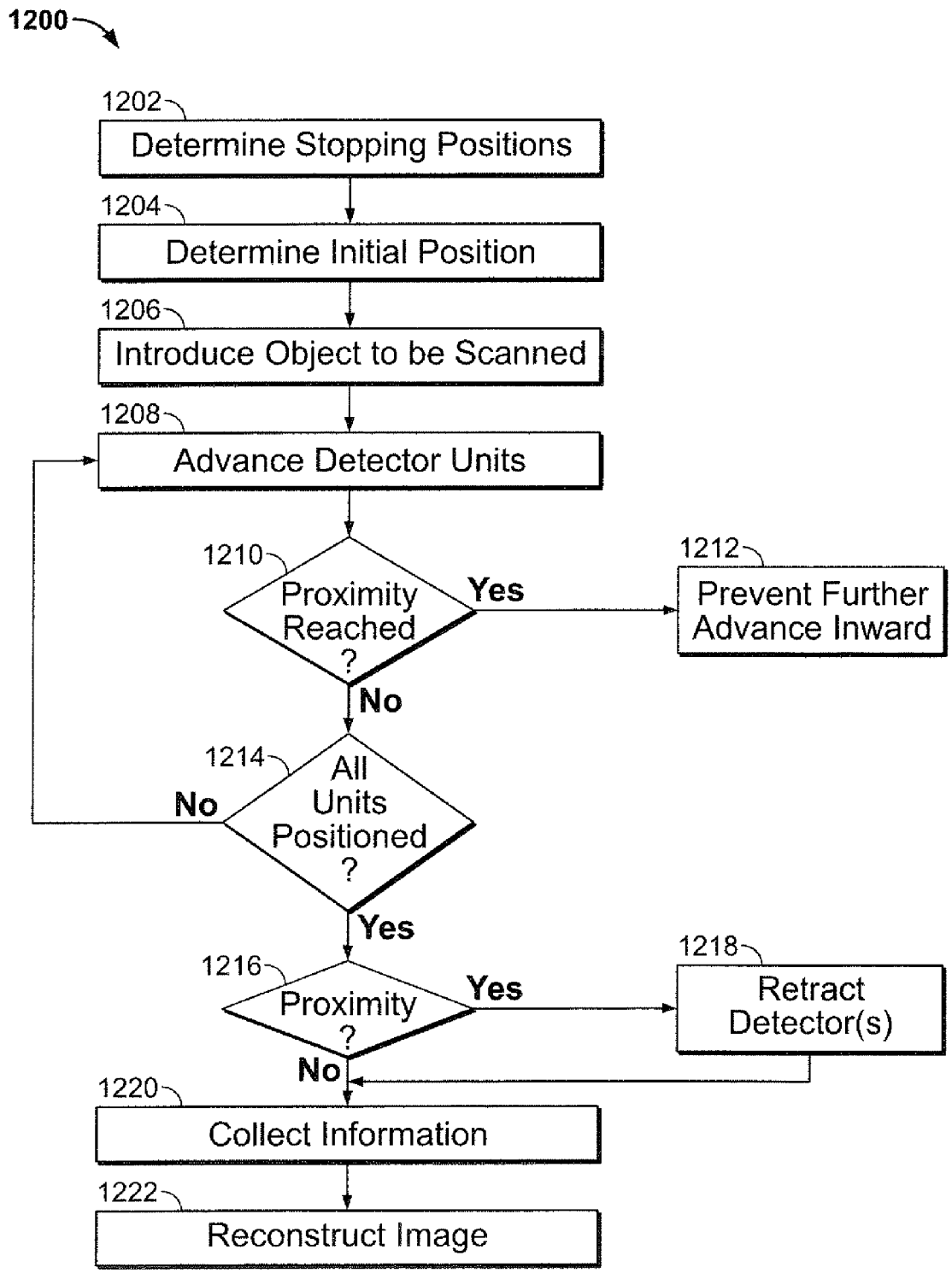
FIG. 12 is a flowchart of a method in accordance with an embodiment.

FIG. 12 provides a flowchart of a method 1200 for imaging an object (e.g., a portion of a human or animal patient) in accordance with various embodiments. The method 1200, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1200 may be able to be used as one or more algorithms to direct hardware to perform one or more operations described herein.

At 1202, stopping positions are determined for each of the detectors. The detectors may be radially distributed about a bore of a gantry. In various embodiments, the detectors may be divided into groups, with the detectors of a given group assigned a common intermediate stopping position past which the detectors of the given group are prevented or inhibited from further radial advancement. The stopping positions may be configured as rings, with the positioning of the rings (e.g., the radii of the rings) and the number of detectors stopped at a given ring determined based on the number of detectors, the spacing of the detectors, and the size of the detectors. The radii of a given ring may be determined by adding an offset, safety margin, or clearance margin to the radius of a ring at which a given number of detectors would contact each other.

At 1204, an initial position for detector units is determined. For example, the detector units may begin at an initial position with each detector unit at a maximum distance radially from a center of a bore of a gantry about which the detector units are radially disposed. As another example, detector units may be positioned at their stop rings or further inwardly and moved outward as patient is advanced. For instance, in some embodiments, each detector may be positioned at the stop ring assigned to a group including the particular detector at the initial position and moved radially outward as appropriate to accommodate a patient. For the example embodiment discussed below, the detector units will be considered as starting from an initial position at which each detector unit is disposed a maximum distance radially from the center of the bore (e.g., the exterior position 300 depicted in FIG. 3.)

Returning to FIG. 12, at 1206, with each the detectors initially in the exterior position an object to be scanned is introduced into the bore. For example, a human patient may be placed on a bed which is translated into the bore.

At 1208, the detector units are advanced toward the assigned rings. For example, in various embodiments for which the detector units start at a maximum radially outward position, the detector units may be advanced radially inward together at about the same speed, with each detector unit stopping at the stopping position or ring assigned to the detector unit. A detector unit in various embodiments may be understood as reaching a given ring when the center of the detector unit is at a distance from the center of the bore that equals the radius of the given ring.

At 1210, it is determined if any detector unit has contacted the object to be imaged or a support structure (e.g., bed or table) or come within a predetermined proximity to the object or support structure. For example, each detector unit may include one or more proximity, pressure, or other sensor device used to sense or detect when the detector unit contacts or comes within a threshold distance of an object to be scanned or a structure. For any detector unit that has reached a predetermined proximity with the object or structure, the method proceeds to 1212. At 1212, the detector unit(s) for which proximity has been reached are prevented from further radially inward advancement. For detector units not proximate to the object or structure, the method 1200 proceeds to 1214.

At 1214, it is determined if all detector units are positioned, either due to proximity with a patient or structure, or due to reaching an assigned stopping position. If all detectors have not reached a stop position, the method proceeds to 1208 and any detectors not stopped due to proximity or pre-assigned position are advanced toward the next radially inward ring or position. If all detector units are positioned or stopped, the method proceeds to 1216.

At 1216, it is determined if the object being imaged has moved such that the object is now in contact with or within a threshold distance of any detector units. If the object is in contact with or within a threshold distance of the object or structure, the method 1200 proceeds to 1218 and the detector unit(s) within proximity are retracted a predetermined distance. If not, the method proceeds to 1220.

At 1220, the detectors are operated to collect imaging information (e.g., NM imaging information such as SPECT imaging information). In various embodiments, only those detectors within a given distance or range of a portion of a patient to be imaged may be utilized to collect imaging information with other detectors idle during the collection of imaging information. At 1222, an image is reconstructed using the information collected at 1220.

Figure 13:
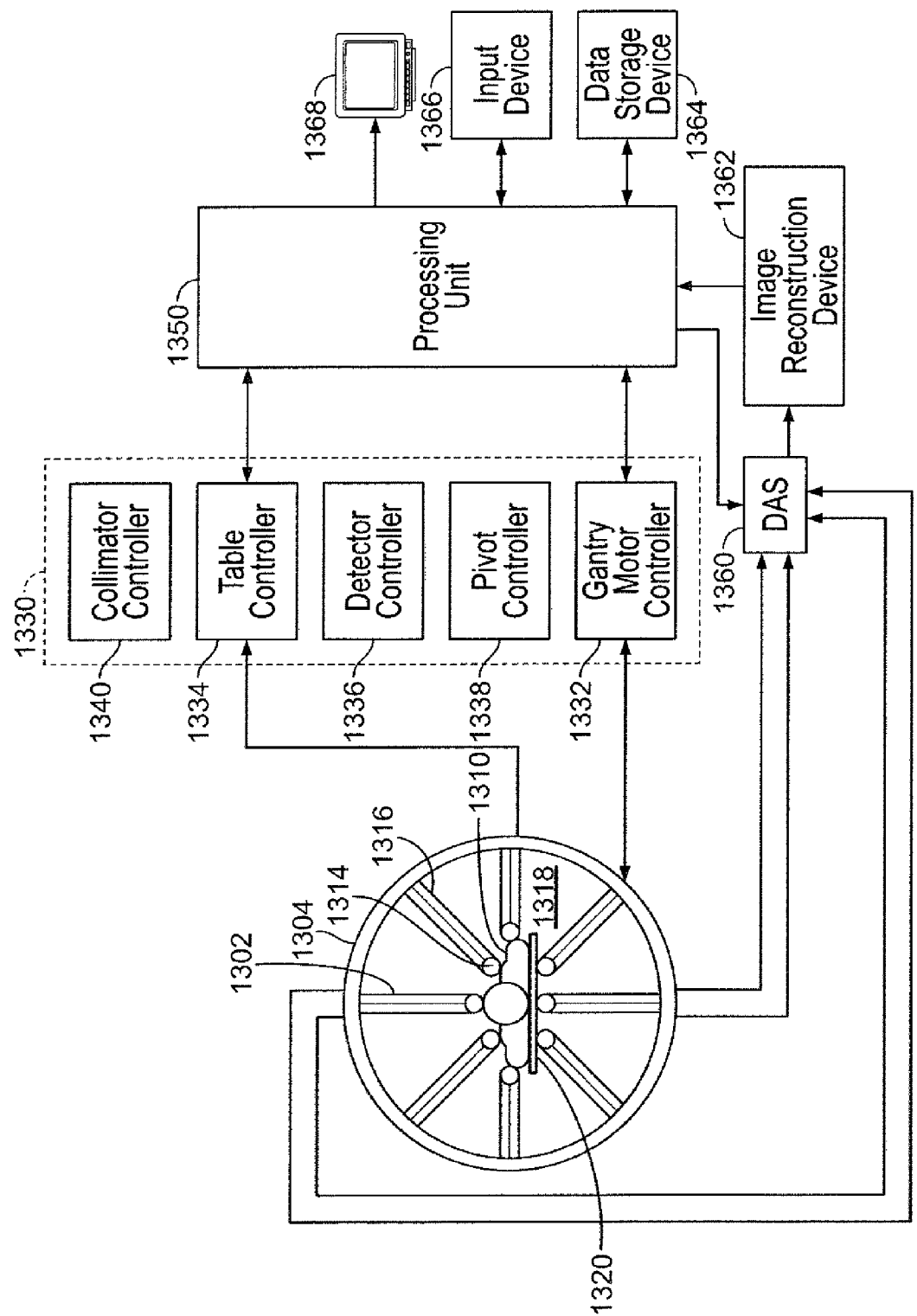
FIG. 13 is a schematic block diagram of a Nuclear Medicine (NM) imaging system in accordance with an embodiment.

FIG. 13 is a schematic illustration of a NM imaging system 1300 having a plurality of imaging detectors mounted on a gantry (which may be mounted, for example, in an iris shape). In particular, a plurality of imaging detectors 1302 are mounted to a gantry 1304. In the illustrated embodiment, the imaging detectors 1302 are disposed radially about a subject 1310 (e.g., a patient), as viewed in FIG. 13. The detectors 1302 may be coupled directly to the gantry 1304, or may be coupled via support members (not shown) to the gantry 1304. Additionally, each of the imaging detectors 1302 includes a detector unit 1314, at least some of which are mounted to a movable detector carrier 1316 (e.g., a support arm or actuator that may be driven by a motor to cause movement thereof) that extends from the gantry 1304. In the illustrated embodiment, the detector carriers 1316 allow movement of the detector units 1314 towards and away from the subject 1310 radially.

Each of the imaging detectors 1302 in various embodiments are smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1302 may include one or more detector units 1314 coupled to a respective detector carrier 1316 and having dimensions of 4 cm to 20 cm and may be formed of Cadmium Zinc Telluride (CZT) tiles or modules. For example, each of the detector units 1314 may be 8×8 cm in size and be composed of a plurality of CZT pixelated modules (not shown). For example, each module may be 4×4 cm in size and have 16×16=256 pixels. In some embodiments, each detector unit 1314 includes a plurality of modules, such as an array of 1×7 modules. However, different configurations and array sizes are contemplated including, for example, detector units 1314 having multiple rows of modules.

It should be understood that the imaging detectors 1302 may be different sizes and/or shapes with respect to each other, such as square, rectangular, circular or other shape. An actual field of view (FOV) of each of the imaging detectors 1302 may be directly proportional to the size and shape of the respective imaging detector.

The gantry 1304 may be formed with an aperture 1318 (e.g., opening or bore) therethrough as illustrated. A patient table 1320, such as a patient bed, is configured with a support mechanism (not shown) to support and carry the subject 1310 in one or more of a plurality of viewing positions within the aperture 1318 and relative to the imaging detectors 1302. Alternatively, the gantry 1304 may comprise a plurality of gantry segments (not shown), each of which may independently move a support member or one or more of the imaging detectors 1302.

The gantry 1304 may also be configured in other shapes, such as a "C", "H" and "L", for example, and may be rotatable about the subject 1310. For example, the gantry 1304 may be formed as a closed ring or circle, or as an open arc or arch which allows the subject 1310 to be easily accessed while imaging and facilitates loading and unloading of the subject 1310, as well as reducing claustrophobia in some subjects 1310.

Additional imaging detectors (not shown) may be positioned to form rows of detector arrays or an arc or ring around the subject 1310. By positioning multiple imaging detectors 1302 at multiple positions with respect to the subject 1310, such as along an imaging axis (e.g., head to toe direction of the subject 1310) image data specific for a larger FOV may be acquired more quickly.

Each of the imaging detectors 1302 has a radiation detection face, which is directed towards the subject 1310 or a region of interest within the subject. The radiation detection faces are each covered by or have coupled thereto a collimator (not shown). The actual FOV for each of the imaging detectors 1302 may be increased, decreased, or relatively unchanged by the type of collimator.

A controller unit 1330 may control the movement and positioning of the patient table 1310, imaging detectors 1302 (which may be configured as one or more arms), gantry 1304 and/or the collimators (that move with the imaging detectors 1d02 in various embodiments, being coupled thereto). The controller unit 1330 and/or processing unit 1350 may be similar in at least certain aspects and/or include some or all of the functionality of the controller 130 described herein. A range of motion before or during an acquisition, or between different image acquisitions, is set to maintain the actual FOV of each of the imaging detectors 1302 directed, for example, towards or "aimed at" a particular area or region of the subject 1310 or along the entire subject 1310. The motion may be a combined or complex motion in multiple directions simultaneously, concurrently, or sequentially as described in more detail herein.

The controller unit 1330 may have a gantry motor controller 1332, table controller 1334, detector controller 1336, pivot controller 1338, and collimator controller 1340. The controllers 1330, 1332, 1334, 1336, 1338, 1340 may be automatically commanded by a processing unit 1350, manually controlled by an operator, or a combination thereof. The gantry motor controller 1332 may move the imaging detectors 1302 with respect to the subject 1310, for example, individually, in segments or subsets, or simultaneously in a fixed relationship to one another. For example, in some embodiments, the gantry controller 1332 may cause the imaging detectors 1302 and/or support members to move relative to or rotate about the subject 1310, which may include motion of less than or up to 180 degrees (or more).

The table controller 1334 may move the patient table 1320 to position the subject 1310 relative to the imaging detectors 1302. The patient table 1320 may be moved in up-down directions, in-out directions, and right-left directions, for example. The detector controller 1336 may control movement of each of the imaging detectors 1302 to move together as a group or individually. The detector controller 1336 also may control movement of the imaging detectors 1302 in some embodiments to move closer to and farther from a surface of the subject 1310, such as by controlling translating movement of the detector carriers 1316 radially towards or away from the subject 1310 (e.g., sliding or telescoping movement) as discussed herein.

The pivot controller 1338 may control pivoting or rotating movement of the detector units 1314 at ends of the detector carriers 1316 and/or pivoting or rotating movement of the detector carrier 1316. For example, one or more of the detector units 1314 or detector carriers 1316 may be rotated about at least one axis to view the subject 1310 from a plurality of angular orientations to acquire, for example, 3D image data in a 3D SPECT or 3D imaging mode of operation. The collimator controller 1340 may adjust a position of an adjustable collimator, such as a collimator with adjustable strips (or vanes) or adjustable pinhole(s).

It should be noted that motion of one or more imaging detectors 1302 may be in directions other than strictly radially, and motions in several motion directions may be used in various embodiment. Therefore, the term "motion controller" may be used to indicate a collective name for all motion controllers. It should be noted that the various controllers may be combined, for example, the detector controller 1336 and pivot controller 1338 may be combined to provide the different movements described herein.

Prior to acquiring an image of the subject 1310 or a portion of the subject 1310, the imaging detectors 1310, gantry 1304, patient table 1320 and/or collimators may be adjusted as discussed in more detail herein, such as to first or initial imaging positions, as well as subsequent imaging positions. The imaging detectors 1302 may each be positioned to image a portion of the subject 1310. Alternatively, one or more of the imaging detectors 1302 may not be used to acquire data, such as the imaging detectors 1302 at one or more exterior stopping positions or rings. Positioning may be accomplished automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1314 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1302, gantry 1304, patient table 1320, and/or collimators are positioned, one or more images, such as three-dimensional (3D) SPECT images are acquired using one or more of the imaging detectors 1302, which may include using a combined motion that reduces or minimizes spacing between detector units 1314. The image data acquired by each imaging detector 1302 may be combined and reconstructed into a composite image or 3D images in various embodiments.

In one embodiment, at least one of the gantry 1304, patient table 1320, and/or collimators are moved after being initially positioned, which includes individual movement of one or more of the detector units 1314 (e.g., combined radial and pivoting movement). Thus, in various embodiments, a plurality of small sized detectors, such as the detector units 1314 may be used for 3D imaging, such as when moving or sweeping the detector units 1314 in combination with other movements.

In various embodiments, a data acquisition system (DAS) 1360 receives electrical signal data produced by the imaging detectors 1302 and converts this data into digital signals for subsequent processing. However, in various embodiments, digital signals are generated by the imaging detectors 1302. An image reconstruction device 1362 (which may be a processing device or computer) and a data storage device 1364 may be provided in addition to the processing unit 1350. It should be noted that one or more functions related to one or more of data acquisition, motion control, data processing and image reconstruction may be accomplished through hardware, software and/or by shared processing resources, which may be located within or near the imaging system 1300, or may be located remotely. Additionally, a user input device 1366 may be provided to receive user inputs (e.g., control commands), as well as a display 1368 for displaying images.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
a plurality of detector units distributed about a bore, the bore configured to accept an object to be imaged, the detector units radially articulable within the bore; and a controller operably coupled to the plurality of detector units and configured to control the positioning of the detector units, wherein the controller is configured to position an external group of the plurality of detector units at a predetermined intermediate position corresponding to a ring, the ring having a radius corresponding to a total number of detector units and a size of the detector units, and to position an internal group of the plurality of detector units radially inside the ring, wherein the imaging system is configured to acquire imaging information of the object to be imaged using at least some of the external group of detectors at the intermediate position and at least some of the detectors of the internal group positioned radially inside the ring.

2. The imaging system of claim 1, wherein the controller is configured to position plural groups of the detector units at corresponding plural intermediate positions, at least one of the intermediate positions configured to accommodate twice as many detector units as an internally adjacent position.

3. The imaging system of claim 1, wherein each of the detector units is configured to pivot about a detector axis parallel to the bore to be swept over a range during image acquisition.

4. The imaging system of claim 1, wherein the ring of the intermediate position corresponds to a radial position at which the detector units contact each other.

5. The imaging system of claim 4, wherein the radius of the ring of the intermediate position is larger by a predetermined offset than a radius of the radial position at which the detector units contact each other.

6. The imaging system of claim 1, wherein the controller is configured to position the detector units from an initial position at which at least some of the detector units are disposed internally of the ring of the intermediate position.

7. The imaging system of claim 1, wherein the controller is configured to position the detector units from an initial position at which each of the detector units are disposed externally of the ring of the intermediate position.

8. The imaging system of claim 7, wherein the controller is configured to advance each of the detector units simultaneously from the initial position to the intermediate position.

9. The imaging system of claim 1, wherein the controller is configured to advance at least one of the external group of detector units radially inwardly of the intermediate position after the internal group of detector units has been advanced radially inwardly of the intermediate position.

10. The imaging system of claim 1, further comprising a plurality of sensing devices corresponding to the plurality of detector units, the sensing devices configured to detect proximity of the detector units to the object being scanned, the controller operably coupled to the sensing devices and configured to retract one of the detector units when a corresponding sensing device senses the object within a threshold distance of the one of the detector units.

11. A method for positioning a plurality of detector units within a bore of an imaging system, the detector units radially articulable within the bore, the method comprising:
positioning an external group of the plurality of detector units at a predetermined intermediate position corresponding to a ring, the ring having a radius corresponding to a total number of detector units and a size of the detector units;
positioning an internal group of the plurality of detector units radially inside the ring; and
acquiring imaging information of an object to be imaged using at least some of the external group of detector units at the intermediate position and at least some of the detector units of the internal group positioned radially inside the ring.

12. The method of claim 11, further comprising moving at least one of the detector units from an initial position at which the at least one of the detector units is disposed radially internally of an imaging position.

13. The method of claim 11, further comprising sensing, with at least one sensing device, proximity of at least one detector unit to the object being scanned within a threshold distance, and retracting the at least one of the detector units a predetermined distance.

14. The method of claim 11, further comprising advancing at least one of the external groups radially inward past the predetermined intermediate position after the internal group has been advanced radially inside the ring.

15. The method of claim 11, further comprising positioning plural groups of the detector units at corresponding plural intermediate positions, at least one intermediate position configured to accommodate twice as many detector units as an internally adjacent position.

16. The method of claim 11, wherein the ring of the intermediate position corresponds to a radial position at which the detectors units contact each other.

17. The method of claim 11, further comprising adjusting at least one of a height or a lateral position of a table upon which an object to be imaged is supported.

18. A tangible and non-transitory computer readable medium configured for positioning a plurality of detector units within a bore of an imaging system, the detector units radially articulable within the bore, the tangible and non-transitory computer readable medium comprising one or more computer software modules configured to direct one or more processors to:
position an external group of the plurality of detector units at a predetermined intermediate position corresponding to a ring, the ring having a radius corresponding to a total number of detector units and a size of the detector units;
position an internal group of the plurality of detector units radially inside the ring;
acquire imaging information of an object to be imaged using at least some of the external group of detector units at the intermediate position and at least some of the detector units of the internal group positioned radially inside the ring.

19. The tangible and non-transitory computer readable medium of claim 18, wherein the computer readable medium is further configured to direct the one or more processors to move at least one of the detector units from an initial position at which the at least one of the detector units is disposed radially internally of an imaging position.

20. The tangible and non-transitory computer readable medium of claim 18, wherein the computer readable medium is further configured to direct the one or more processors to obtain proximity information from at least one sensing device indicating proximity of at least one detector unit to the object being scanned within a threshold distance, and to retract the at least one of the detector units a predetermined distance responsive to obtaining the proximity information.

21. The tangible and non-transitory computer readable medium of claim 18, wherein the ring of the intermediate position corresponds to a radial position at which the detectors units contact each other.

22. The imaging system of claim 1, wherein the controller is configured to position the internal group to define an internal ring of detectors, to position the external group to define an external ring, and to position at least one intermediate group to define at least one intermediate ring interposed between the external ring and the internal ring of detectors.

23. The imaging system of claim 22, wherein the controller is configured to advance a given detector radially inward until:
   (1) the given detector is within a predetermined distance of the object to be imaged or a support structure; or
   (2) the given detector has reached a corresponding predetermined ring of the external ring, the internal ring, or the at least one intermediate ring.

24. The imaging system of claim 22, wherein a corresponding ring for a given detector is determined using $\rho=1$ for $n=(2k)$ for $k=0, 1, 2, 3, \ldots N/2$, $\rho=2$ for $n=(3+4k)$ for $k=0, 1, 2, 3, \ldots (N-4)/4$, $\rho=3$ for $n=(5+8k)$ for $k=0, 1, 2, 3, \ldots (N-8)/8$, and $\rho=4$ for $n=(9+16k)$ for $k=0, 1, 2, 3, \ldots (N-16)/16$, where N=a total number of detectors,
   n=an identifying number for the given detector, and $\rho$ is the corresponding ring for the given detector, with higher values of $\rho$ disposed radially inward of lower values of $\rho$.

* * * * *